United States Patent [19]

Horrobin

[11] Patent Number: 5,080,909
[45] Date of Patent: Jan. 14, 1992

[54] ANTI-VIRAL COMPOSITIONS
[75] Inventor: David F. Horrobin, Nova Scotia, Canada
[73] Assignee: Efamol Limited, Surrey, England
[21] Appl. No.: 429,601
[22] Filed: Oct. 31, 1989

Related U.S. Application Data

[63] Continuation of Ser. No. 159,128, Feb. 23, 1988, Pat. No. 4,886,670, which is a continuation of Ser. No. 60,857, Jun. 12, 1987, abandoned, which is a continuation of Ser. No. 939,965, Dec. 10, 1986, abandoned, which is a continuation of Ser. No. 846,094, Mar. 31, 1986, abandoned, which is a continuation of Ser. No. 743,394, Jun. 11, 1985, abandoned, which is a continuation of Ser. No. 628,270, Jul. 6, 1984, abandoned.

[30] Foreign Application Priority Data

Jul. 27, 1983 [GB] United Kingdom ............... 8320203

[51] Int. Cl.$^5$ .................. A61K 33/14; A61K 31/22
[52] U.S. Cl. .................................... 424/677; 514/46
[58] Field of Search ........................... 514/46; 424/677

[56] References Cited

PUBLICATIONS

Chemical Abstracts 93:89318a (1980).
Merck Index, 9th Ed., Merck & Co. IWC., Rahway, N.J., 1976 p. App-3.

Primary Examiner—Stanley J. Friedman
Attorney, Agent, or Firm—Foley & Lardner

[57] ABSTRACT

The anti-viral effectiveness of conventional anti-viral agents such as acyclovir, idoxuridine, vidarabine etc. is enhanced by formulation or administration with a physiologically acceptable lithium salt.

7 Claims, No Drawings

ANTI-VIRAL COMPOSITIONS

This application is a continuation, of application Ser. No. 07/159,128, filed Feb. 23, 1988 now U.S. Pat. No. 4,886,670, which is a continuation of Ser. No. 060,857, filed June 12, 1987 abandoned; which is a continuation of Ser. No. 939,965, filed Dec. 10, 1986 abandoned; which is a continuation of Ser. No. 846,094, filed Mar. 31, 1986 abandoned; which is a continuation of Ser. No. 743,394, filed June 11, 1985 abandoned; which is a continuation of Ser. No. 628,270, filed July 6, 1984 now abandoned.

This invention relates to novel compositions which be used for the treatment of viral infections in man and animals, as well as to a method of such treatment.

A large number of compounds have been found to exhibit in vitro anti-viral activity but only a few of these compounds have so far been found to be active in vivo. Examples of compounds which have been found to be active, to varying degrees of success, in the treatment of viral infections include amantadine, interferons, isoprinosine, cytarabine, idoxuridine, vidarabine and acyclovir. However, it has been found that viruses are capable of developing resistance to many of the anti-viral agents currently in use. For example, concern has recently been expressed in the medical literature over the emergence of strains of herpes simplex viruses which are resistant to acyclovir.

The in vitro ability of lithium compounds to prevent viral replication, notably of DNA viruses, at concentrations which do not destroy host cells has been described by Skinner et al., Med. Microbiol. Immunol. 168, 139-48, 1980. I have found that topically applied lithium-containing compositions are highly effective in reducing the pain and irritation associated with herpes virus infections such as cold sores and genital herpes. The nature of the anion associated with the lithium ion in such compositions does not appear to be important, provided of course that the anion is physiologically acceptable and permits bioavailability of the lithium ions.

I have now surprisingly found that viruses do not become resistant to lithium compounds on repeated exposure thereto. This implies that the mechanism for anti-viral activity of lithium differs from the mechanism for the activity of the known anti-viral agents. In order to reduce the risk of the emergence of resistant viral strains, I therefore propose the conjoint use of a lithium compound with one or more other anti-viral compounds in the treatment of viral infections, since it is unlikely that the infecting virus would become resistant where the mechanisms for anti-viral activity of the compounds differ. I also believe that the conjoint administration of the compounds will increase anti-viral activity.

In one aspect, therefore, the invention provides a pharmaceutical composition comprising as active ingredients an effective amount of at least one physiologically acceptable lithium salt together with an effective amount of at least one other anti-viral compound.

In another aspect, the invention provides a method for the treatment of a viral infection in a human or warm-blooded animal subject which comprises conjointly administering to said subject an effective amount of least one physiologically acceptable lithium salt together with an effective amount of at least one other anti-viral compound.

Lithium salts have been safely used for many years in the treatment of manic-depressive psychosis, the lithium salt being orally administered in an amount sufficient to maintain a blood lithium ion concentration of the order of 0.8 to 1 millimolar. However, such concentrations are generally not sufficient to exhibit a significant level of anti-viral activity, since it has been found that higher lithium ion concentrations are generally required to inhibit viral replication. Thus, in the method of the invention anti-virally effective blood lithium ion concentrations may be achieved by oral or parenteral administeration without inducing any serious toxicity problems, as the body may be able to tolerate for short periods much higher concentrations of lithium than would be acceptable in the treatment of manic depression, where administration may be necessary over many years or even decades.

The invention is however particularly preferred for the treatment of viral infections by topical administration of the lithium salt with the other anti-viral agent(s). In this way, local concentrations of lithium ions sufficient to be lethal to the infecting virus may be achieved without unduly raising the blood lithium ion concentration. I have for example, found that on topical administration of a lithium containing composition for up to 7 days, the plasma concentration of lithium is consistently less than 0.1 millimolar. This indicates that the use of lithium salts in topical compositions is very safe, and this safety, coupled with my discovery of the ability of lithium to block viral replication without inducing resistance, makes lithium particularly suitable for combination with other anti-viral agents.

Examples of other anti-viral agents which may be used in the compositions and method according to the invention include amantadine, interferons, isoprinosine, cytarabine, idoxuridine, vidarabine and acyclovir. These compounds may be incorporated into compositions according to the invention in anti-virally effective amounts, e.g. amounts as known in the art, and advantageously make up from 0.01 to 30%, preferably 0.2 to 10%, by weight of the compositions.

Any physiologically acceptable lithium salt may be used according to the invention since, as indicated above, the nature of the anion in the salt is not believed to be important. Examples of such salts include lithium chloride, succinate, citrate, acetylsalicylate and orotate. The compositions for use according to the invention conveniently contain from 0.01 to 30%, and preferably 0.2 to 5%, by weight of lithium ions.

Compositions according to the invention may conveniently take the form of, for example, tablets, capsules, solutions, emulsions, syrups, suspensions, lotions, creams, ointments, gels, powders and suppositories. As indicated above, compositions adapted for topical administration are particularly preferred.

Viral infections which may be treated according to the invention include, for example, those due to herpes simplex or herpes zoster viruses. In particular, topical administration according to the invention may be used in the treatment of herpes labialis, herpes genitalis or shingles.

I have established that lithium salts do not cause the emergence of resistant virus strains by determining dose-response curves for the action of lithium ions against type-2 herpes simplex virus in baby hamster kidney cells. Viral replication is barely detectable at lithium concentrations of 24 millimolar and does not occur at concentrations above that figure. In my studies, the virus was therefore passaged through lithium by inoculating layers of baby hamster kidney cells and culturing for 48 hours in the presence of a medium containing 6, 12 or 24 millimolar lithium ions. The monolayers were then washed, harvested and virus yields estimated by a plaque technique. Passage was repeated 15 times in lithium chloride. At the end of this time sensitivity of the virus to lethal concentrations of lithium ions was tested. The virus was found to be just as sensitive as before passage, thus indicating that there had been no development of resistance. Similar results were obtained using a strain of type-1 herpes simplex virus.

I have also found that when patients are topically treated with lithium succinate ointment for recurrent genital herpes infections, there is no evidence of the development of resistance in virus harvested from the lithium-treated lesions on the 4th or 5th day of infection and tested against lithium in vitro.

The following examples serve to illustrate compositions according to the invention. All percentages are by weight.

EXAMPLE 1

Ointment

| | |
|---|---|
| Acyclovir | 5% |
| Lithium succinate | 8% |
| Lanolin base | 87% |

EXAMPLE 2

Aqueous Cream

| | |
|---|---|
| Idoxuridine | 10% |
| Lithium citrate | 10% |
| Aqueous cream base | 80% |

EXAMPLE 3

Lotion

| | |
|---|---|
| Acyclovir | 10% |
| Lithium chloride | 12% |

-continued

| | |
|---|---|
| Lotion base | 78% |

EXAMPLE 4

Aqueous cream

| | |
|---|---|
| Interferon | 1% |
| Lithium acetylsalicylate | 6% |
| Aqueous cream base | 93% |

EXAMPLE 5

Ointment

| | |
|---|---|
| Vidarbine | 5% |
| Lithium succinate | 7% |
| Lanolin base | 88% |

I claim:

1. A pharmaceutical composition comprising as active ingredients an effective synergistic amount of at least one physiologically acceptable lithium salt together with an anti-virally effective amount of vidarabine.

2. A composition as claimed in claim 1 wherein said lithium salt is selected from the group consisting of lithium chloride, lithium succinate, lithium citrate, lithium acetylsalicylate and lithium orotate.

3. A composition as claimed in claim 1 containing from 0.01 to 30% by weight of lithium ions.

4. A composition as claimed in claim 1 containing from 0.2 to 10% by weight of vidarabine.

5. A method for the treatment of a viral infection in a human or warm-blooded animal subject which comprises conjointly administering to said subject an effective synergistic amount of at least one physiologically acceptable lithium salt together with an anti-virally effective amount of vidarabine.

6. A method as claimed in claim 5 wherein said lithium salt is selected from the group consisting of lithium chloride, lithium succinate, lithium citrate, lithium acetysalicylate and lithium orotate.

7. A method as claimed in claim 5 wherein said lithium salt and vidarabine are topically administered to herpes lesions.

* * * * *